United States Patent
Goodsell et al.

(10) Patent No.: US 10,383,969 B1
(45) Date of Patent: Aug. 20, 2019

(54) ELEMENTS FOR DISPERSING FRAGRANCE

(71) Applicant: Rimports, LLC, Provo, UT (US)

(72) Inventors: Jeffrey Alan Goodsell, Springville, UT (US); Alan K. Farrell, Salt Lake City, UT (US); Lamar Thompson, Montgomery, AL (US); Wu Jingqing, Huizhou (CN)

(73) Assignee: Rimports, LLC—A Sterno Group Company, Provo, UT (US)

( * ) Notice: Subject to any disclaimer, the term of this patent is extended or adjusted under 35 U.S.C. 154(b) by 0 days.

(21) Appl. No.: 15/628,523

(22) Filed: Jun. 20, 2017

Related U.S. Application Data

(63) Continuation-in-part of application No. 14/690,145, filed on Apr. 17, 2015, now Pat. No. 9,867,896, and a continuation of application No. 14/328,701, filed on Jul. 11, 2014, now Pat. No. 9,682,164.

(60) Provisional application No. 61/981,369, filed on Apr. 18, 2014, provisional application No. 61/981,013, filed on Apr. 17, 2014, provisional application No. 62/016,161, filed on Jun. 24, 2014.

(51) Int. Cl.
*A61L 9/04* (2006.01)
*A61L 9/12* (2006.01)

(52) U.S. Cl.
CPC ............... *A61L 9/122* (2013.01); *A61L 9/04* (2013.01)

(58) Field of Classification Search
CPC .... A61L 9/03; A61L 9/04; A61L 9/122; B01F 3/04
USPC .......... 261/94, 95, DIG. 88; 239/60
See application file for complete search history.

(56) References Cited

U.S. PATENT DOCUMENTS

| | | | |
|---|---|---|---|
| 4,059,422 A | 11/1977 | Steiner | |
| 4,666,638 A | 5/1987 | Baker et al. | |
| 4,707,338 A | 11/1987 | Spector | |
| 5,192,342 A | 3/1993 | Baron et al. | |
| 5,230,867 A | 7/1993 | Kunze et al. | |

(Continued)

FOREIGN PATENT DOCUMENTS

| | | |
|---|---|---|
| CN | 203489149 U | 3/2014 |
| EP | 0925717 A1 | 6/1999 |

(Continued)

OTHER PUBLICATIONS

ScentSavvy, Scent Savvy Flameless Candlelight Scent Set—Silver, Gold, http://www.samsclub.com/sams/fragrancers/prod11140158.ip, Jan. 7, 2011, 2 pages.

(Continued)

*Primary Examiner* — Robert A Hopkins
(74) *Attorney, Agent, or Firm* — Durham Jones & Pinegar, P.C., Intellectual Property Law Group

(57) ABSTRACT

A fragrance delivery element may be configured to generate one or more vortices as air flows therethrough. The fragrance delivery element may include one or more airflow apertures, each of which may be configured to receive airflow and convert the airflow to a vortex. As air flows through each airflow aperture and past the fragrance delivery element, fragrance is emitted into the air. Emission of the fragrance may occur without heating the fragrance delivery element or the fragrance. The creation of at least one vortex may extend the distance fragrance is thrown from the fragrance delivery element. Methods and systems for dispersing fragrance are also disclosed.

19 Claims, 2 Drawing Sheets

(56) References Cited

U.S. PATENT DOCUMENTS

| | | |
|---|---|---|
| 5,376,338 A | 12/1994 | Zlotnik |
| 5,431,885 A | 7/1995 | Zlotnik et al. |
| 5,460,787 A | 10/1995 | Colon |
| 5,498,397 A | 3/1996 | Horng |
| 5,547,616 A | 8/1996 | Dancs et al. |
| 5,565,148 A | 10/1996 | Pendergrass |
| 7,223,166 B1 | 5/2007 | Wiseman et al. |
| 7,942,388 B2 | 5/2011 | Suissa et al. |
| 8,137,629 B2 | 3/2012 | Faber et al. |
| 8,158,066 B2 | 4/2012 | Yang et al. |
| 8,412,029 B2 | 4/2013 | Browder et al. |
| 8,724,975 B2 | 5/2014 | Browder et al. |
| 2003/0035729 A1 | 2/2003 | Chen |
| 2003/0086815 A1 | 5/2003 | Wesley |
| 2007/0025888 A1 | 2/2007 | Gupte et al. |
| 2007/0207066 A1 | 9/2007 | Thur et al. |
| 2008/0130266 A1 | 6/2008 | DeWitt et al. |
| 2009/0200393 A1 | 8/2009 | Avelar |
| 2010/0001417 A1 | 1/2010 | D'Amico |
| 2010/0044468 A1 | 2/2010 | Granger et al. |
| 2011/0027124 A1 | 2/2011 | Albee et al. |
| 2012/0183280 A1* | 7/2012 | Kowalec .............. A61L 9/03 392/386 |
| 2013/0049236 A1 | 2/2013 | Garon et al. |
| 2015/0297774 A1 | 10/2015 | Thompson et al. |

FOREIGN PATENT DOCUMENTS

| | | |
|---|---|---|
| EP | 0962139 A1 | 12/1999 |
| EP | 2287089 A1 | 2/2011 |
| JP | H111216335 A | 8/1999 |
| WO | 1995010352 A1 | 4/1995 |
| WO | 2012093246 A1 | 7/2012 |

OTHER PUBLICATIONS

International Search Report and Written Opinion, International application No. PCT/US2015/026490, Jun. 25, 2015, 15 pages.
International Preliminary Report on Patentability, International application No. PCT/US2015/026490, Oct. 27, 2016, 12 pages.

* cited by examiner

ELEMENTS FOR DISPERSING FRAGRANCE

CROSS REFERENCE TO RELATED APPLICATIONS

This application is a continuation of U.S. patent application Ser. No. 14/328,701, filed on Jul. 11, 2014, titled ELEMENTS FOR DISPERSING FRAGRANCE ("the '701 Application"), now U.S. Pat. No. 9,682,164, issued on Jun. 20, 2017. This application is also a continuation-in-part of U.S. patent application Ser. No. 14/690,145, filed on Apr. 17, 2015, titled FRAGRANCE DELIVERY SYSTEM, DEVICES, AND METHODS ("the '145 Application"), now U.S. Pat. No. 9,867,896, issued on Jan. 16, 2018. The '145 Application claims the benefit of priority to the Jun. 24, 2014 filing date of U.S. Provisional Patent Application No. 62/016,160, titled FRAGRANCE DELIVERY SYSTEM ("the '160 Provisional Application"), to the Apr. 18, 2014 filing date of U.S. Provisional Patent Application No. 61/981,369, titled FRAGRANCE DELIVERY SYSTEM ("the '369 Provisional Application"), and to the Apr. 17, 2014 filing date of U.S. Provisional Patent Application No. 61/981,013, titled FRAGRANCE DELIVERY SYSTEM ("the '013 Provisional Application"). The entire disclosure of each of the '701 Application, the '145 Application, the '160 Provisional Application, the '369 Provisional Application, and the '013 Provisional Application is hereby incorporated herein.

TECHNICAL FIELD

This disclosure relates generally to apparatuses for dispersing fragrance and, more specifically, to apparatuses for dispersing fragrance without heat.

DISCLOSURE

In one aspect, this disclosure relates to fragrance delivery elements, from which fragrance may be dispersed without added heat. Such a fragrance delivery element may comprise a body formed from a carrier, with fragrance dispersed throughout at least a portion of the carrier. The carrier may comprise a polymer. In a specific, but non-limiting embodiment, the polymer from which the body of a fragrance delivery element is formed may comprise ethylene vinyl acetate (EVA). An oil-based fragrance may be dispersed throughout a fragrance delivery element that comprises EVA. The fragrance may initially comprise about five percent (5%) to about twenty percent (20%) of the weight of the fragrance delivery element.

A fragrance delivery element according to this disclosure may be configured to enable air to pass or flow therethrough, and to generate at least one vortex from the airflow. Accordingly, such a fragrance delivery element may include a plurality of airflow apertures that are configured to interact with an airflow incident with the fragrance delivery element in a manner that generates one or more vortices. The airflow apertures formed through a fragrance delivery element may be configured to receive airflow from an airflow generating unit (e.g., a fan, etc.) at one side (e.g., at a base side, etc.) of the fragrance delivery element, and to convert that airflow into one or more vortices on an opposite side (e.g., a top, etc.) of the fragrance delivery element. In a specific embodiment, each airflow aperture through the fragrance delivery element may be located and, optionally, bend along a circle that is concentric with the fragrance delivery element. In a more specific embodiment, each airflow aperture may be twisted in a manner that provides the desired effect when air flows through that aperture, and collectively through all of the apertures of the fragrance delivery element. Even more specifically, all of the airflow apertures may be oriented in the same manner.

The arrangement of the airflow apertures relative to one another (e.g., across the fragrance delivery element, etc.) may also be configured to provide for airflow in a desired manner. As an example, the airflow apertures may be configured to provide one or more vortices that will optimize or otherwise tailor the direction and/or distance that fragrance may be thrown from the fragrance delivery element. In some embodiments, each airflow aperture may generate a vortex, which may transport a fragrance captured in the airflow (i.e., fragrance emitted from the material of the body of the fragrance delivery element) a greater distance than the airflow would on its own, and with less of the fragrance being dispersed than the dispersal that would occur without the vortex. In some embodiments, a plurality of airflow apertures may generate parallel vortices that circulate in the same direction. These vortices may combine to form a larger vortex.

A specific embodiment of fragrance delivery element according to this disclosure includes a body that has a shape that resembles a disk. More specifically, such a fragrance delivery element may include a raised central area. A raised central area may place an increased quantity of fragrance in the path of airflow from a fan or other airflow-generating unit, or at a location where the airflow is strongest, or is most concentrated, which may optimize the rate at which fragrance is released from the fragrance delivery element. In some embodiments, the fragrance delivery element may be shaped as a dome, with a flat base and a convex top surface that includes an exterior periphery adjacent to an exterior periphery of the base.

A fragrance delivery element may optionally include a positioning aperture, which may be configured to receive a positioning element that protrudes from a surface on which the fragrance delivery element is to be positioned. In embodiments where the fragrance delivery element is configured as a dome, the positioning aperture may comprise a central aperture that extends along a height of the dome. The central aperture may be cylindrical in shape, and may define an interior periphery of the base of the body, the top of the body and the remainder of the body. In such an embodiment, the fragrance delivery element may be configured as a halo.

In another aspect, this disclosure relates to systems for dispersing fragrance. Such a system may include a base, a unit for generating airflow, such as a fan, associated with the base and a fragrance delivery element configured to be carried by the base and to receive airflow from the unit for generating airflow. The fragrance delivery element may be configured to receive airflow, emit fragrance into the airflow, and generate one or more vortices from the airflow. Transference of the fragrance from the fragrance delivery element to the airflow may be effected without heat. A system for dispersing fragrance may include a decorative container for the fragrance delivery element, as well as an optional light for illuminating the fragrance delivery element.

Methods for dispersing fragrance are also disclosed. Such a method includes generating one or more fragrance-containing vortices in airflow that delivers the fragrance to one or more intended locations.

Other aspects, as well as features and advantages of various aspects, of the disclosed subject matter will become apparent to those of ordinary skill in the art through consideration of the ensuing description, the accompanying drawings, and the appended claims.

DETAILED DESCRIPTION

Figure 1:
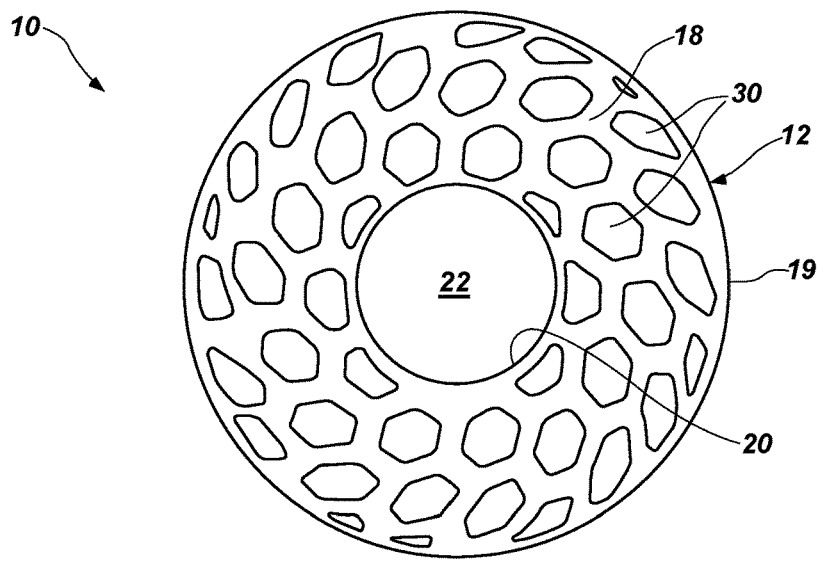
FIG. 1 is a top view of an embodiment of fragrance delivery element according to this disclosure, which includes a plurality of airflow apertures that are oriented and configured to generate one or more vortices.
Figure 2:
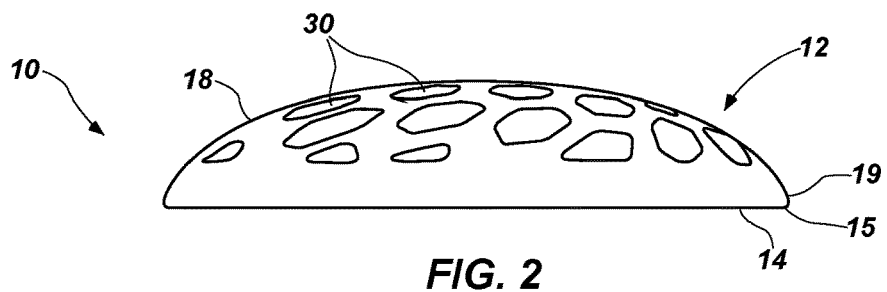
FIG. 2 is a side view of the embodiment of fragrance delivery element shown in FIG. 1.
Figure 3:
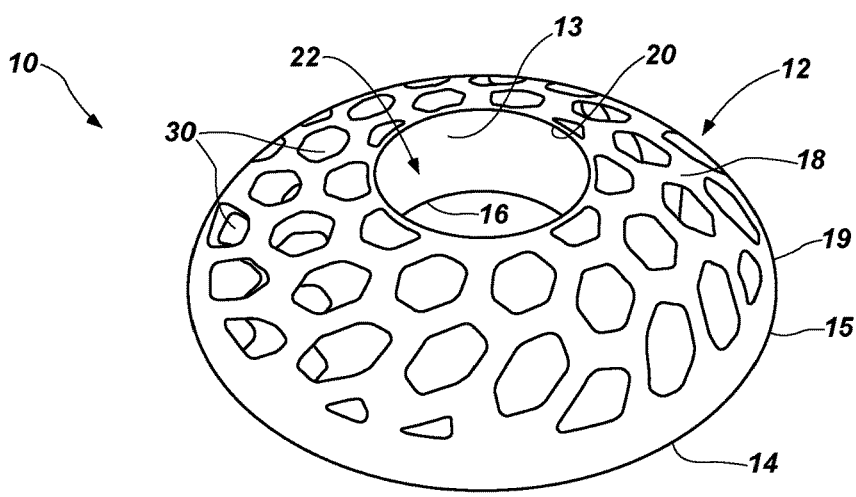
FIG. 3 is a perspective view of the embodiment of fragrance delivery element shown in FIG. 1.

FIGS. 1 through 4 depict a specific, but non-limiting embodiment of a fragrance delivery element 10 according to this disclosure. The fragrance delivery element 10 includes a body 12 with a base 14 and a top surface 18. As shown in FIG. 2, the base 14 of the body 12 is flat, while the top surface 18 has a convex configuration that imparts the body 12 with a dome-like configuration. More specifically, in the orientation of the body 12 depicted by FIG. 2, at its outer periphery 19, the top surface 18 extends upwardly from the outer periphery 15 of the base 14, and then gradually extends in a more horizontal orientation toward a center of the body 12.

As illustrated by FIGS. 1 through 4, a fragrance delivery element 10 may also include a positioning aperture 22. The positioning aperture 22 is defined by interior peripheries 13, 16 and 20 of the body 12, base 14 and top surface 18, respectively. In the depicted embodiment, the positioning aperture 22 is located centrally and has a cylindrical shape. Of course, other locations and configurations of positioning apertures 22 are also within the scope of this disclosure.

A plurality of airflow apertures 30 are defined through the body 12 of the fragrance delivery element 10. The airflow apertures 30 may be configured to enable airflow incident with a first surface of the body 12 (e.g., its base 14, etc.) to be communicated to another, second surface of the body 12 (e.g., its top surface 18, etc.). In addition, at least one, some or even all of the airflow apertures 30 are oriented and configured to generate one or more vortices as air flows therethrough.

Figure 4:
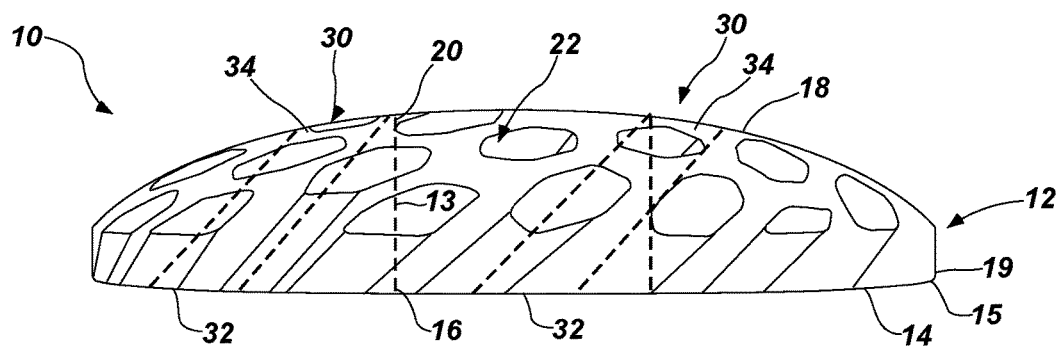
FIG. 4 is a cross-sectional view of the embodiment of fragrance delivery element shown in FIG. 1, illustrating an embodiment of the orientation and configuration of an airflow aperture that is configured to receive airflow from a rotary fan and to generate at least one vortex from that airflow.

In the specific, but non-limiting embodiment depicted by FIGS. 1 through 4, and with specific reference to FIG. 4, an airflow aperture 30 may be oriented at a non-perpendicular angle to the base 14 of the body 12. In embodiments where the fragrance delivery element 10 includes a plurality of airflow apertures 30, the airflow apertures 30 may be arranged in such a way that each airflow aperture 30 receives air in substantially the same manner as at least one other airflow aperture 30. In the illustrated embodiment, which is configured to receive airflow from a fan (not shown in FIGS. 1 through 4) with a blade that rotates clockwise, the airflow apertures 30 are positioned around the body 12, and the orientation of each airflow aperture 30 is based on the location of that airflow aperture 30 around the body 12. The airflow apertures 30 may, as illustrated, be oriented at angles that, from the bottom 32 of each airflow aperture 30 to the top 34 of each airflow aperture 30, collectively extend in a counter-clockwise arrangement. Even more specifically, each airflow aperture 30 may be oriented at a 45° angle to the base 14 of the body 12 of the fragrance delivery element 10.

In some embodiments, each airflow aperture 30 has a cross-sectional configuration that, taken transverse to a length or height of that airflow aperture 30, is polygonal (e.g., the illustrated hexagonal cross-sectional configuration, other regular polygons, irregular polygons, etc.). Of course, embodiments of airflow apertures 30 that have circular cross-sectional configurations, other round cross-sectional configurations and multi-sided cross-sectional configurations with one or more curved sides are also within the scope of this disclosure.

One or more of the airflow apertures 30 may also have a twisted configuration. The twisted configuration of an airflow aperture 30 may generate desired airflow patterns, such as vortices. In the depicted embodiment, each airflow aperture 30 is twisted, from the bottom 32 of that airflow aperture 30 to its top 34, in a counter-clockwise direction.

Figure 5:
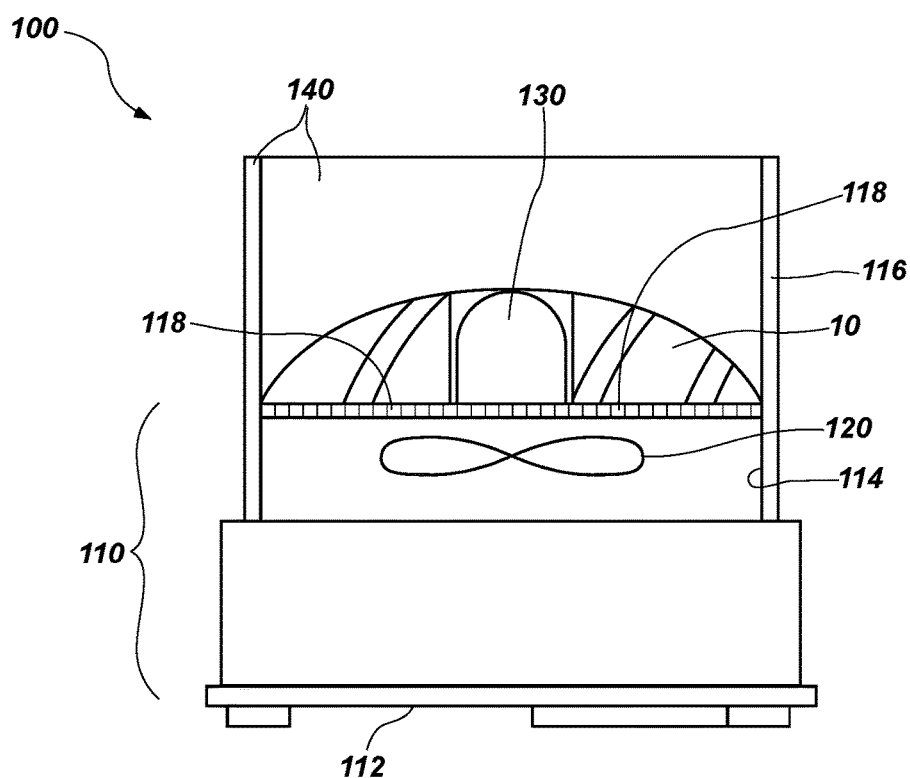
FIG. 5 provides a cross-sectional representation of an embodiment of a system for dispersing fragrance.

Turning now to FIG. 5, an embodiment of a system 100 for dispersing fragrance is depicted. That system 100 includes a base 110 with a bottom 112, top 116 and an interior 114 located between the bottom 112 and the top 116. In addition, the system 100 includes at least one fragrance delivery element 10. Optionally, the system 100 may also include a decorative container 140.

The bottom 112 of the base 110 is configured to be supported by a surface, such as a tabletop, a countertop, or the like. The interior 114 of the base 110 carries a unit for generating airflow, such as a fan 120, and at least some of the associated electronic circuitry and/or componentry associated with that unit (e.g., the fan 120, etc.), such as a power supply and wiring. Other electronic componentry associated with the fan 120, such as a switch, a power port, etc., may also be carried by the base 110, but be accessible from an exterior of the base 110. The top 116 of the base 110 may include one or more vents 118 through which airflow generated by the fan 120 may pass. In addition, the top 116 of the base 110 may be configured to support a fragrance delivery element 10.

In some embodiments, the base 110 may also include a light 130. At least some of the electronic circuitry and/or componentry associated with the light 130 may be carried within the interior 114 of the base 110, while the light 130 may be visible from the top 116 of the base 110. The light 130 may illuminate the fragrance delivery element 10 and/or a decorative container 140 positioned over the base 110 and the fragrance delivery element 10 without heating the fragrance delivery element 10 or any other element of the system 100. Without limitation, the light 130 may comprise one or more light-emitting diodes (LEDs).

As illustrated by FIG. 5, the light 130 may protrude from the top 116 of the base 110. A fragrance delivery element 10 that is configured for use with such a base 110 may include a positioning aperture 22 (see FIGS. 1 and 2) configured to receive a light 130 or any other positioning element that protrudes from the top 116 of the base 110.

In various embodiments, a system 100 for dispersing fragrance may be configured to do so without applying heat to the fragrance delivery element 10. Accordingly, such a system 100 may consist essentially of a unit for generating airflow, such as a fan 120 and the base 110 that houses the fan 120, and a fragrance delivery element 10. Such a system may non-essentially include an illumination element, such as the light 130 and/or a decorative container 140. In some embodiments, a system 100 may consist of the foregoing elements.

Although the foregoing disclosure provides many specifics, these should not be construed as limiting the scope of any of the appended claims, but merely as providing information pertinent to some specific embodiments that may fall within the scopes of the claims. Other embodiments may be devised which lie within the scopes of the claims. Features from different embodiments may be employed in any combination. All additions, deletions and modifications, as disclosed herein, that fall within the scopes of the claims are to be embraced by the claims.

What is claimed:

1. A fragrance delivery element, comprising:
    a body comprising a polymer matrix impregnated with a fragrance, the body including a base and a top; and
    a plurality of apertures extending through the body, from the base of the body to the top of the body, apertures of the plurality of apertures being oriented and arranged to create a vortex above the top of the body from air flowing from the base of the body, through the apertures, and out of the top of the body.

2. The fragrance delivery element of claim 1, wherein each aperture of the plurality of apertures is oriented at a non-perpendicular angle relative to the base of the body.

3. The fragrance delivery element of claim 1, wherein all apertures of the plurality of apertures are oriented at a same angle relative to the base.

4. The fragrance delivery element of claim 1, wherein each aperture of the plurality of apertures curves from the base of the body to the top of the body.

5. The fragrance delivery element of claim 1, wherein each aperture of the plurality of apertures is oriented in alignment with a circumference of at least one circle in concentric alignment with the body.

6. The fragrance delivery element of claim 1, wherein the base of the body is flat.

7. The fragrance delivery element of claim 6, wherein the top of the body is curved.

8. The fragrance delivery element of claim 7, wherein the body has a dome shape.

9. The fragrance delivery element of claim 8, further comprising:
    cylindrical aperture located at a center of the dome shape and extending through a height of the dome shape, the cylindrical aperture imparting the body with a halo configuration.

10. A system for delivering fragrance, comprising:
    a base including an upper surface;
    a fan associated with the base, the fan configured to direct airflow in a predetermined rotational direction past the upper surface of the base; and
    a fragrance delivery element configured to be positioned on the base, the fragrance delivery element including:
        a body comprising a polymer matrix impregnated with a fragrance, the body including a base and a top; and
        a plurality of apertures extending through the body, from the base of the body to the top of the body, the body configured to release the fragrance without added heat.

11. The system of claim 10, wherein the plurality of apertures are collectively oriented and arranged to receive the airflow from the fan at the base of the body and to create a vortex above the top of the body.

12. The system of claim 11, wherein each aperture of the plurality of apertures is oriented at a non-perpendicular angle relative to the base of the body.

13. The system of claim 10, further comprising:
    a decorative container for the fragrance delivery element.

14. The system of claim 13, further comprising:
    a light for illuminating the decorative container without heating the fragrance delivery element.

15. The system of claim 14, wherein:
    at least a portion of the light protrudes from the base; and
    the fragrance delivery element is configured to receive at least the portion of the light.

16. A method for distributing fragrance, comprising:
    directing airflow into and through apertures in a body of a fragrance delivery element; and
    an arrangement and orientation of the apertures generating a vortex from the airflow, the vortex including fragrance emitted by the body of the fragrance delivery element.

17. The method of claim 16, wherein generating the vortex comprises enhancing a throw of the fragrance.

18. The method of claim 16, wherein directing airflow comprises directing airflow at an ambient temperature through the apertures in the body of the fragrance delivery element.

19. The method of claim 16, further comprising:
    orienting the fragrance delivery element in such a way that the apertures are aligned with a direction of the airflow.

* * * * *